(12) United States Patent
Alvarez

(10) Patent No.: US 11,572,175 B2
(45) Date of Patent: *Feb. 7, 2023

(54) ENCLOSED SPACE OCCUPANCY DETECTION SYSTEMS AND METHODS

(71) Applicant: THE BOEING COMPANY, Chicago, IL (US)

(72) Inventor: Christopher Alvarez, Burien, WA (US)

(73) Assignee: THE BOEING COMPANY, Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 17/140,049

(22) Filed: Jan. 2, 2021

(65) Prior Publication Data

US 2021/0122470 A1    Apr. 29, 2021

Related U.S. Application Data

(63) Continuation of application No. 16/202,470, filed on Nov. 28, 2018, now Pat. No. 10,906,647.

(51) Int. Cl.
| | | |
|---|---|---|
| *G08B 21/22* | (2006.01) | |
| *B64D 11/02* | (2006.01) | |
| *B64F 5/30* | (2017.01) | |
| *A61L 2/10* | (2006.01) | |

(Continued)

(52) U.S. Cl.
CPC ............. *B64D 11/02* (2013.01); *A61L 2/10* (2013.01); *A61L 2/24* (2013.01); *B64D 45/00* (2013.01); *B64F 5/30* (2017.01); *G08B 21/22* (2013.01); *A61L 2202/11* (2013.01); *A61L 2202/14* (2013.01); *A61L 2202/25* (2013.01); *B64D 2045/007* (2013.01)

(58) Field of Classification Search
CPC . A61B 1/00; G08B 1/00; G08B 21/22; B64D 11/02; B64D 45/00; B64D 2045/007; A61L 2/10; A61L 2/24; A61L 2202/11; A61L 2202/14; A61L 2202/25
See application file for complete search history.

(56) References Cited

U.S. PATENT DOCUMENTS

| | | | | |
|---|---|---|---|---|
| 2005/0264414 A1* | 12/2005 | Sweeney | ................ | G08B 19/00 340/567 |
| 2012/0320215 A1* | 12/2012 | Maddi | .................... | H04N 7/183 348/E5.085 |
| 2016/0220716 A1* | 8/2016 | Childress | ............... | B64D 11/02 |

(Continued)

*Primary Examiner* — Hongmin Fan
(74) *Attorney, Agent, or Firm* — The Small Patent Law Group LLC; Joseph M. Butscher

(57) ABSTRACT

An occupancy detection system and method for an enclosed space includes a door sensor operatively coupled to a door of the enclosed space. The door sensor is configured to output a door sensor signal that indicates a status of the door. At least one presence sensor that is configured to output at least one presence sensor signal that indicates an occupancy status of the enclosed space. An occupancy detection control unit is in communication with the door sensor and the at least one presence sensor. The occupancy detection control unit is configured to receive the door sensor signal and the presence sensor signal(s). The occupancy detection control unit is configured to determine an occupancy status of the enclosed space based on the door sensor signal and the presence sensor signal(s).

27 Claims, 8 Drawing Sheets

(51) Int. Cl.
*A61L 2/24* (2006.01)
*B64D 45/00* (2006.01)

(56) References Cited

U.S. PATENT DOCUMENTS

| | | | | |
|---|---|---|---|---|
| 2016/0273986 A1* | 9/2016 | Neubarth | ............... | G01L 9/0073 |
| 2017/0290935 A1* | 10/2017 | Boodaghians | ........ | A47L 7/0061 |
| 2019/0240362 A1* | 8/2019 | Corsetti | .................... | A61L 9/20 |

* cited by examiner

ENCLOSED SPACE OCCUPANCY DETECTION SYSTEMS AND METHODS

RELATED APPLICATIONS

This application is a continuation of U.S. patent application Ser. No. 16/202,470, entitled "Lavatory Occupancy Detection Systems and Methods," filed Nov. 28, 2018, now U.S. Pat. No. 10,906,647, which is hereby incorporated by reference in its entirety.

FIELD OF THE DISCLOSURE

Embodiments of the present disclosure generally relate to occupancy detection systems and methods for enclosed spaces, such as lavatories, which may be used within interior cabins of commercial aircraft.

BACKGROUND OF THE DISCLOSURE

Commercial aircraft transport passengers between locations. A typical commercial aircraft includes at least one lavatory within an interior cabin. During a flight, passengers may use the lavatory. In order to prevent or otherwise reduce lines for the lavatory, a sign proximate to the lavatory indicates whether the lavatory is occupied or unoccupied. When the door of the lavatory is locked, the sign indicates that the lavatory is occupied. That is, an individual within the lavatory locking the lavatory door causes a sign proximate to the lavatory to indicate that the lavatory is occupied.

However, an individual within the lavatory may neglect to lock the lavatory door. In this situation, the sign indicates that the lavatory is unoccupied even through the individual is within the lavatory. In short, an individual within the lavatory typically needs to affirmatively perform a specific task, in particular locking the door, to indicate that the lavatory is occupied.

Further, ultraviolet (UV) cleaning systems that are configured to sanitize components within lavatories are currently being developed. Cleaning cycles for certain UV cleaning systems may be three seconds or less. An indication of occupancy of a lavatory within an aircraft via a passenger locking/unlocking a door is typically delayed. For example, the time from the passenger unlocking a lavatory door to an indication that the lavatory is no longer occupied may be a few seconds. However, a cleaning process may not commence until the lavatory is determined to be unoccupied.

SUMMARY OF THE DISCLOSURE

A need exists for a system and method for accurately determining whether or not a lavatory, such as within a commercial aircraft, is occupied. Further, a need exists for a system and method for determining the occupancy of a lavatory without an individual performing a specific task to indicate such occupancy. Moreover, a need exists for a system and method for quickly and efficiently determining an occupancy status of a lavatory.

With those needs in mind, certain embodiments of the present disclosure provide an occupancy detection system for a lavatory. The occupancy detection system includes a door sensor operatively coupled to a door of the lavatory. The door sensor is configured to output a door sensor signal that indicates a status of the door. At least one presence sensor is configured to output at least one presence sensor signal that indicates an occupancy status of the lavatory. An occupancy detection control unit is in communication with the door sensor and the presence sensor(s). The occupancy detection control unit is configured to receive the door sensor signal and the presence sensor signal(s). The occupancy detection control unit is configured to determine an occupancy status of the lavatory based on the door sensor signal and the at least one presence sensor signal.

In at least one embodiment, the occupancy detection control unit determines that the lavatory is unoccupied in response to the door sensor signal indicating that the door is open. The occupancy detection control unit determines that the occupancy status is occupied in response to the door sensor signal indicating that the door is closed and the presence signal(s) indicating that an individual is within the lavatory. In at least one embodiment, the door sensor signal indicating that the door is open triggers the occupancy detection control unit to perform a reading of the presence signal(s). The occupancy detection control unit resets the occupancy status to unoccupied in response to the door sensor signal indicating that the door is opened after being closed.

In at least one embodiment, the door sensor includes one or more of a proximity sensor, a pressure sensor, or a temperature sensor. For example, the presence sensor(s) includes one or more of a proximity sensor, a pressure sensor, or a temperature sensor.

In at least one embodiment, the at least one presence sensor includes a floor sensor operatively coupled to a floor of the lavatory, and the at least one presence sensor signal includes a floor sensor signal output by the floor sensor. As an example, the at least one presence sensor includes a changing table sensor operatively coupled to a changing table of the lavatory, and the at least one presence sensor signal includes a changing table sensor signal output by the changing table sensor. As another example, the at least one presence sensor includes a toilet sensor operatively coupled to a toilet of the lavatory, and the at least one presence sensor signal includes a toilet sensor signal output by the toilet sensor. In at least one embodiment, the at least one presence sensor includes a plurality of presence sensors including a floor sensor operatively coupled to a floor of the lavatory (the at least one presence sensor signal includes a floor sensor signal output by the floor sensor), a changing table sensor operatively coupled to a changing table of the lavatory (the at least one presence sensor signal further includes a changing table sensor signal output by the changing table sensor), and a toilet sensor operatively coupled to a toilet of the lavatory (the at least one presence sensor signal further comprises a toilet sensor signal output by the toilet sensor).

In at least one embodiment, the occupancy detection system also includes an occupancy indicator. The occupancy detection control unit is in communication with the occupancy indicator. The occupancy status of the lavatory is indicated by the occupancy indicator.

In at least one embodiment, the occupancy detection system also includes a cleaning system that is in communication with the occupancy detection control unit. The cleaning system is configured to automatically clean at least a portion of the lavatory when the door is closed and the lavatory is unoccupied.

In at least one embodiment, the occupancy detection control unit is configured to respond to receiving the door sensor signal and the at least one presence sensor signal by transmitting a control signal to one or more switches to actuate the switches from a closed state to an open state to deactivate one or more components of a light control system. In at least one embodiment, in response to a UV light source being deactivated, the occupancy detection control unit deactivates a cleaning indication of an occupancy indicator.

Certain embodiments of the present disclosure provide an occupancy detection method for a lavatory. The occupancy detection method includes operatively coupling a door sensor to a door of the lavatory, communicatively coupling an occupancy detection control unit with the door sensor and at least one presence sensor of the lavatory, outputting, by the door sensor, a door sensor signal that indicates a status of the door, outputting, by the at least one presence sensor, at least one presence sensor signal that indicates an occupancy status of the lavatory, receiving, by the occupancy detection control unit, the door sensor signal and the at least one presence sensor signal, and determining, by the occupancy detection control unit, an occupancy status of the lavatory based on the door sensor signal and the at least one presence sensor signal.

In at least one embodiment, the determining includes determining that the lavatory is unoccupied in response to the door sensor signal indicating that the door is open. For example, the determining includes determining that the occupancy status is occupied in response to the door sensor signal indicating that the door is closed and the at least one presence sensor signal indicating that an individual is within the lavatory. In at least one embodiment, the occupancy detection method includes triggering, by the door sensor signal indicating that the door is open, the occupancy detection control unit to perform a reading of the at least one presence sensor signal. In at least one embodiment, the occupancy detection method includes resetting, by the occupancy detection control unit, the occupancy status to unoccupied in response to the door sensor signal indicating that the door is opened after being closed.

In at least one example, the occupancy detection method includes communicatively coupling an occupancy indicator with the occupancy detection control unit, and indicating the occupancy status of the lavatory by the occupancy indicator.

In at least one embodiment, the occupancy detection method includes communicatively coupling a cleaning system with the occupancy detection control unit, and automatically cleaning at least a portion of the lavatory when the door is closed and the lavatory is unoccupied.

In at least one embodiment, in response to the receiving, transmitting a control signal to one or more switches to actuate the switches from a closed state to an open state to deactivate one or more components of a light control system. In at least one embodiment, in response to one of more components of the light control system being deactivated, deactivating a cleaning indication of an occupancy indicator.

DETAILED DESCRIPTION OF THE DISCLOSURE

Figure 1:
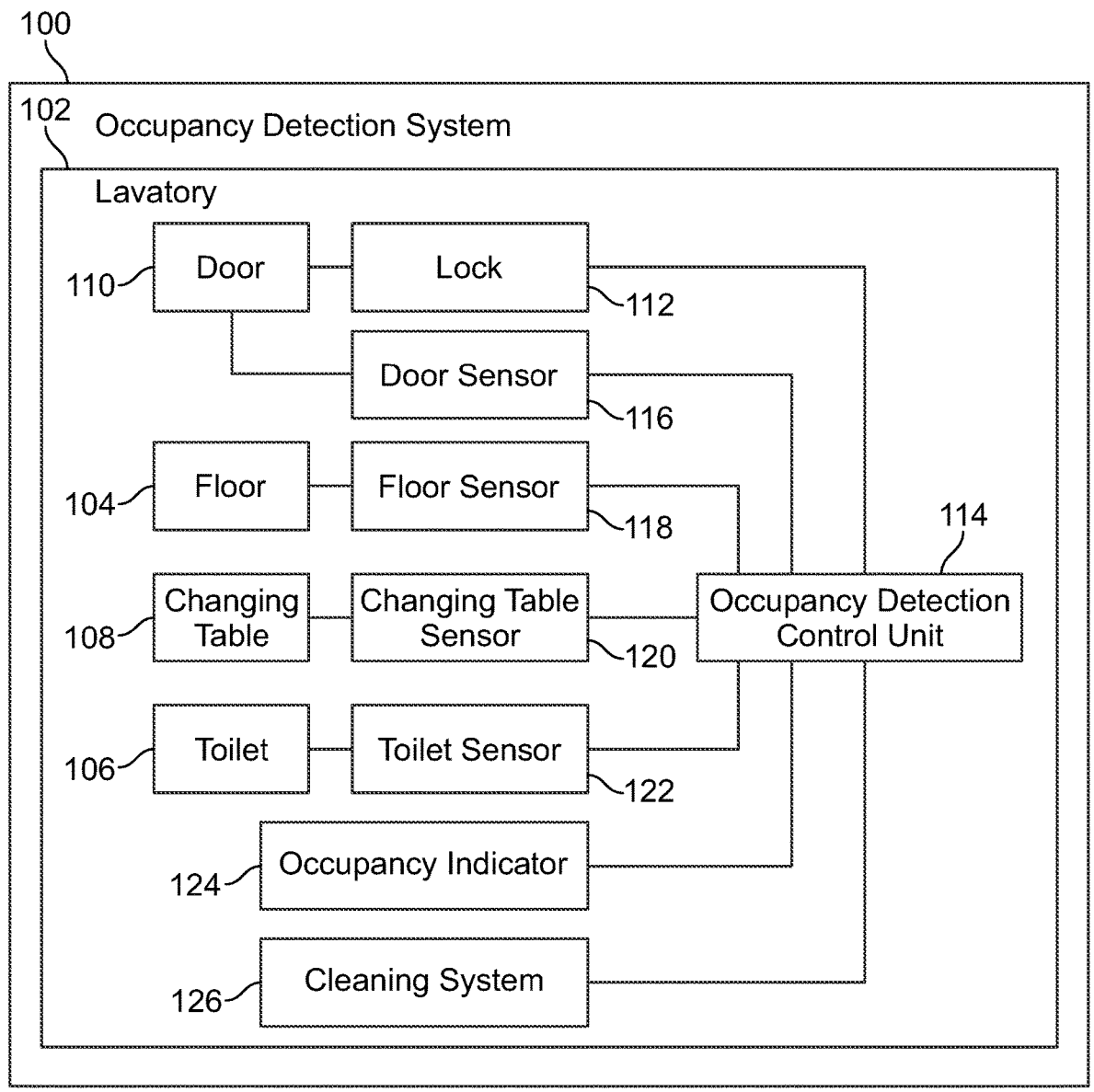
FIG. 1 illustrates a schematic block diagram of an occupancy detection system for a lavatory, according to an embodiment of the present disclosure.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition may include additional elements not having that condition.

Certain embodiments of the present disclosure provide an occupancy detection system and method for a lavatory, such as within a vehicle, such as a commercial aircraft, ship, train, bus, or the like. The occupancy detection system includes an occupancy detection control unit in communication with one or more sensors of the lavatory. The occupancy detection system and method is configured to detect occupancy of a lavatory without an individual performing an affirmative task that would otherwise indicate that the lavatory is occupied. In at least one embodiment, the occupancy detection control unit is configured to receive sensor inputs from the sensor(s) that detect presence of an individual on a floor, toilet seat, or changing table within the lavatory.

In at least one embodiment, in response to a door of the lavatory closing, the occupancy detection control unit detects signals output by the sensor(s). If the sensor(s) indicate a presence of an individual within the lavatory, the occupancy detection control unit outputs an occupied signal to an occupancy indicator, which then indicates that the lavatory is occupied. If the sensor(s) indicate that an individual is not within the lavatory, the occupancy detection control unit outputs an unoccupied signal to the occupancy indicator, which then indicates that the lavatory is unoccupied.

In at least one embodiment, closing of the door triggers a single reading of the sensor(s), instead of continuous monitoring of the sensor(s). Once the sensor(s) have been read, the occupancy detection control unit passes the sensor signals through internal logic gates to determine occupancy status. Until the door is opened, a state is declared that may not be altered. Occupancy may be declared when the door closes and either the floor, toilet seat, or changing table register a presence. Sensor signals may be received from each sensor and put through an AND logic gate. If any one of the sensors registers a presence, the occupancy detection control unit declares that the lavatory is occupied. In at least one embodiment, the occupancy detection system and method is configured to immediately determine an occupancy status of a lavatory without relying on compliance from the occupant.

Certain embodiments of the present disclosure provide an occupancy detection system for a lavatory. The occupancy detection system includes a door sensor operatively coupled to a door of the lavatory. The door sensor is configured to output a door sensor signal that indicates a status of the door. At least one presence sensor is configured to output at least one presence sensor signal that indicates an occupancy status of the lavatory. An occupancy detection control unit is in communication with the door sensor and the presence sensor(s). The occupancy detection control unit is configured to receive the door sensor signal and the presence sensor signal(s). The occupancy detection control unit is configured to determine the occupancy status of the lavatory based on the door sensor signal and the presence sensor signal(s).

FIG. 1 illustrates a schematic block diagram of an occupancy detection system 100 for a lavatory 102, according to an embodiment of the present disclosure. In at least one embodiment, the lavatory 102 is within a vehicle, such as within an interior cabin of a commercial aircraft, ship (cargo ship, cruise ship, or the like), train, bus, and/or the like. In at least one other embodiment, the lavatory 102 is within a fixed structure, such as an office building.

In at least one embodiment, the lavatory 102 or enclosed space includes one or more elements (fixtures) that are intended to be used by a person using the lavatory 102. Examples of these elements include a changing table, a toilet with an attached seat, a bidet, and/or the like. In at least one embodiment, the lavatory 102 includes a floor 104 that supports a toilet 106. A changing table 108 is also within the lavatory 102. A door 110 is at an entrance of the lavatory 102. The door 110 is configured to be opened and closed. A lock 112 is configured to be engaged to selectively lock and unlock the door 110.

An occupancy detection control unit 114 is in communication with one or more sensors that are configured to output sensor signals. In at least one embodiment, the occupancy detection control unit 114 is within the lavatory 102. In at least one other embodiment, the occupancy detection control unit 114 is outside of the lavatory 102.

The occupancy detection control unit 114 is in communication with a door sensor 116, such as through one or more wired or wireless connections. The door sensor 116 is operatively coupled to the door 110. In at least one embodiment, the door sensor 116 is or includes a proximity sensor, a pressure sensor, a temperature sensor, or the like. The door sensor 116 is configured to detect when the door 110 is opened and closed. The door sensor 116 is configured to output a door sensor signal indicating a door status, such as whether the door 110 is opened or closed to the occupancy detection control unit 114.

In at least one embodiment, the occupancy detection control unit 114 is also in communication with one or more presence sensors that output one or more presence signals indicative of an occupancy status of the lavatory 102 (for example, whether or not an individual is within the lavatory 102). For example, the occupancy detection control unit 114 is in communication with a floor sensor 118, such as through one or more wired or wireless connections. The floor sensor 118 is operatively coupled to the floor 104. In at least one embodiment, the floor sensor 118 is or includes a proximity sensor, a pressure sensor, a temperature sensor, or the like. The floor sensor 118 is configured to detect the presence of an individual on the floor 104. For example, the floor sensor 118 is a pressure sensor that detects a weight of the individual standing on the floor 104. The floor sensor 118 is configured to output a floor sensor signal indicating whether an individual is on the floor 104 or not.

In at least one embodiment, the occupancy detection control unit 114 is also in communication with a presence sensor in the form of a changing table sensor 120, such as through one or more wired or wireless connections. The changing table sensor 120 is operatively coupled to the changing table 108. In at least one embodiment, the changing table sensor 120 is a proximity sensor, a pressure sensor, a temperature sensor, or the like. The changing table sensor 120 is configured to detect force (such as weight) on the changing table 108. In at least one other embodiment, the changing table sensor 120 is configured to detect whether the changing table is in an upright stowed position, or an extended position (such as a horizontal position). The changing table sensor 120 is configured to output a changing table sensor signal, which indicates whether or not the changing table is in use (such as being in an extended position).

In at least one embodiment, the occupancy detection control unit 114 is also in communication with a presence sensor in the form of a toilet sensor 122, such as through one or more wired or wireless connections. The toilet sensor 122 is operatively coupled to the toilet 106. In at least one embodiment, the toilet sensor 122 is a proximity sensor, a pressure sensor, a temperature sensor, or the like. The toilet sensor 122 is configured to detect force (such as weight) on the toilet 106. For example, the toilet sensor 122 is a pressure sensor that is configured to detect whether an individual is seated on the toilet 106. The toilet sensor 122 is configured to output a toilet sensor signal indicating whether or not an individual is seated on the toilet 106.

As shown, the occupancy detection control unit 114 is in communication with the door sensor 116 the floor sensor 118, the changing table sensor 120, and the toilet sensor 122. In at least one other embodiment, the occupancy detection system 100 includes less than all three of the floor sensor 118, the changing table sensor 120, and the toilet sensor 122. For example, in at least one embodiment, the occupancy detection control unit 114 is in communication the door sensor 116 and one of the floor sensor 118, the changing table sensor 120, or the toilet sensor 122. In at least one other embodiment, the occupancy detection control unit 114 is in communication with the door sensor 116 and only two of the floor sensor 118, the changing table sensor 120, and the toilet sensor 122. In at least one embodiment, the lavatory 102 does not include the changing table 108.

The occupancy detection control unit 114 is also in communication with an occupancy indicator 124, such as through one or more wired or wireless connections. In at least one embodiment, the occupancy indicator 124 is an illuminated sign that is configured to switch between indications of occupied and unoccupied. In at least one other embodiment, the occupancy indicator is a digital screen, monitor, or the like that shows text and/or video. In at least one embodiment, the occupancy indicator 124 is also configured to indicate that a cleaning process is in progress.

In at least one embodiment, the occupancy detection control unit 114 is also be in communication with a cleaning system 126, such as through one or more wired or wireless connections. In at least one embodiment, the cleaning system 126 is configured to automatically clean at least a portion of the lavatory 102 (such as the toilet 106, a sink, or the like). In at least one embodiment, the cleaning system 126 automatically cleans the portion(s) of the lavatory 102 when the lavatory 102 is unoccupied and the door 110 is closed. In at least one embodiment, the cleaning system 126 includes one or more ultraviolet lights that are configured to sanitize portions of the lavatory 102, such as the toilet 106, a sink (not shown in FIG. 1), or the like through emission of ultraviolet radiation. In at least one other embodiment, the lavatory 102 does not include the cleaning system 126.

In operation, the occupancy detection control unit 114 is configured to detect whether or not the lavatory 102 is occupied through presence sensor signals received from one or more of the floor sensor 118, the changing table sensor 120, and the toilet sensor 122. When the door 110 is in an open state, the door sensor 116 outputs a door sensor signal to the occupancy detection control unit 114 indicating that door 110 is open. In response, the occupancy detection control unit 114 determines that the lavatory is unoccupied, and directs the occupancy indicator 124 to indicate that the lavatory 102 is unoccupied. In one example, the occupancy detection control unit 114 is then in a standby mode, or a hibernation mode in which little or no power is drawn by the occupancy detection control unit 114. For example, in at least one embodiment, the occupancy detection control unit 114 includes one or more flip-flops or switches that are configured to transition between an occupied state and an unoccupied state.

When the door 110 is closed, the door sensor 116 senses the closing of the door 110 and outputs a door sensor signal to the occupancy detection control unit 114 indicating that the door is closed. The door sensor signal indicating that the door 110 is closed triggers the occupancy detection control unit 114 into the occupied state, in which the occupancy detection control unit 114 monitors sensor signals output by the floor sensor 118, the changing table sensor 120, and the toilet sensor 122. If any of the sensor signals output by the floor sensor 118, the changing table sensor 120, or the toilet sensor 122 indicate presence of an individual within the lavatory 102, the occupancy detection control unit 114 determines that the lavatory 102 is occupied, and directs the occupancy indicator 124 to indicate that the lavatory 102 is occupied. The occupancy detection control unit 114 is thus in the occupied state, and returns to standby or hibernation mode as long as the door 110 remains closed.

In at least one embodiment, if, however, the sensor signals indicate that an individual is not within the lavatory 102, the occupancy detection control unit 114 prompts the cleaning system 126 to begin a cleaning process. The occupancy detection control unit 114 then directs the occupancy indicator 124 to indicate that the lavatory 102 is unoccupied (that is, open), but that a cleaning process in progress (for example, via an illuminated cleaning process indicator). The cleaning process indication remains indicated on the occupancy indicator 124 for an entire length of the cleaning process. After the cleaning process is complete, the occupancy indicator 124 turns off the cleaning process indicator. If the door 110 is opened during the cleaning process, the cleaning system 126 immediately ceases the cleaning process. In at least one other embodiment, the occupancy detection control unit 114 locks the door 110 until the cleaning process is complete.

After the door 110 is closed, and the occupancy detection control unit 114 determines whether or not the lavatory 102 is occupied or unoccupied through the received presence sensor signals from the floor sensor 118, the changing table sensor 120, or the toilet sensor 122, the occupancy detection control unit 114 remains in the determined state (whether occupied or unoccupied) until the door 110 is reopened. When the door 110 is reopened, the occupancy detection control unit 114 switches back to (or remains in) the unoccupied state, and thereby indicates on the occupancy indicator 124 that the lavatory 102 is unoccupied (that is, open).

As described, the occupancy detection system 100 for the lavatory 102 includes the door sensor 116 operatively coupled to the door 110 of the lavatory 102. The door sensor 116 is configured to output a door sensor signal that indicates a status (for example, open or closed) of the door 110. At least one presence sensor (such as the floor sensor 118, the changing table sensor 120, or the toilet sensor 122) is configured to output at least one presence sensor signal (such as a floor sensor signal, a changing table sensor signal, or a toilet sensor signal) that indicates an occupancy status (such as occupied or open) of the lavatory 102. The occupancy detection control unit 114 is in communication with the door sensor 116 and the presence sensor(s). The occupancy detection control unit 114 is configured to receive the door sensor signal and the presence sensor signal(s). The occupancy detection control unit 114 is further configured to determine the occupancy status of the lavatory 102 based on the door sensor signal and the presence sensor signal(s).

Figure 2:
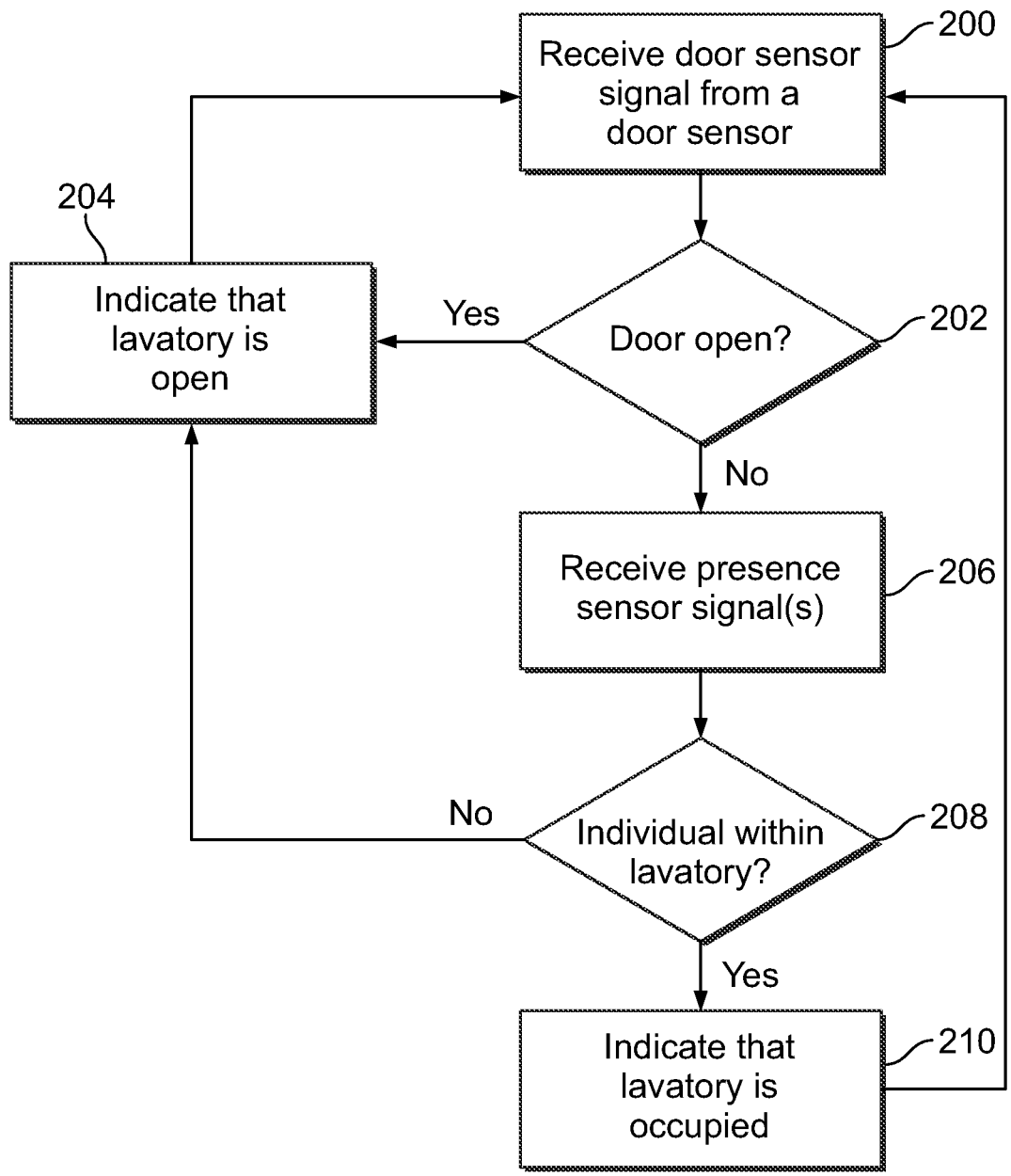
FIG. 2 illustrates a flow chart of an occupancy detection method for a lavatory, according to an embodiment of the present disclosure.

FIG. 2 illustrates a flow chart of an occupancy detection method for a lavatory, according to an embodiment of the present disclosure. Referring to FIGS. 1 and 2, at 200, the occupancy detection control unit 114 receives a door sensor signal from the door sensor 116. The door sensor signal indicates whether the door 110 is opened or closed. At 202, the occupancy detection control unit 114 determines whether the door 110 is open through the received door sensor signal. If the door 110 is opened, the occupancy detection control unit 114 indicates, via the occupancy indicator 124, that the lavatory is open at 204.

If, however, the door 110 is not opened (that is, the door 110 is closed), the occupancy detection control unit 114 receives presence sensor signal(s) 206 from one or more of the floor sensor 118, the changing table sensor 120, or the toilet sensor 122. Examples of the presence sensor signals include the floor sensor signal, the changing table sensor signal, and the toilet sensor signal. The presence sensor signal(s) indicate whether or not an individual is within the lavatory 102. At 208, the occupancy detection control unit determines whether the lavatory 102 is occupied or open through the received presence sensor signal(s). If an individual is not within the lavatory 102, the occupancy detection control unit 114 indicates, via the occupancy indicator 124, that the lavatory 102 is open at 204. If, however, an individual is within the lavatory 102, the occupancy detection control unit 114 indicates, via the occupancy indicator 124, that the lavatory 102 is occupied at 210. The process then returns to 200.

Certain embodiments of the present disclosure provide an occupancy detection method for the lavatory 102. The occupancy detection method includes operatively coupling the door sensor 116 to the door 110 of the lavatory 102; communicatively coupling the occupancy detection control unit 114 with the door sensor 116 and at least one presence sensor of the lavatory 102; outputting, by the door sensor 116, a door sensor signal that indicates a status of the door 110; outputting, by the at least one presence sensor, at least one presence sensor signal that indicates an occupancy status of the lavatory 102; receiving, by the occupancy detection control unit 114, the door sensor signal and the at least one presence sensor signal; and determining, by the occupancy detection control unit 114, an occupancy status of the lavatory 102 based on the door sensor signal and the at least one presence sensor signal.

In at least one embodiment, the determining includes determining that the lavatory 102 is unoccupied in response to the door sensor signal indicating that the door is open. In at least one embodiment, the determining includes determining that the occupancy status is occupied in response to the door sensor signal indicating that the door 110 is closed and the at least one presence sensor signal indicating that an individual is within the lavatory 102. In an example, the occupancy detection method includes triggering, by the door sensor signal indicating that the door 110 is open, the occupancy detection control unit 114 to perform a reading of the at least one presence sensor signal. In at least one embodiment, the occupancy detection method includes resetting, by the occupancy detection control unit 114, the occupancy status to unoccupied in response to the door sensor signal indicating that the door 110 is opened after being closed.

In at least one embodiment, the occupancy detection method includes communicatively coupling the occupancy indicator 124 with the occupancy detection control unit 114, and indicating the occupancy status of the lavatory 102 by the occupancy indicator 124.

In at least one example, the occupancy detection method includes communicatively coupling the cleaning system 126 with the occupancy detection control unit 114, and automatically cleaning at least a portion of the lavatory 102 when the door 110 is closed and the lavatory 102 is unoccupied.

As used herein, the term "control unit," "central processing unit," "unit," "CPU," "computer," or the like includes any processor-based or microprocessor-based system including systems using microcontrollers, reduced instruction set computers (RISC), application specific integrated circuits (ASICs), logic circuits, and any other circuit or processor including hardware, software, or a combination thereof capable of executing the functions described herein. Such are exemplary only, and are thus not intended to limit in any way the definition and/or meaning of such terms. In at least one embodiment, the occupancy detection control unit 114 is or includes one or more processors that are configured to control operation thereof, as described herein.

The occupancy detection control unit 114 is configured to execute a set of instructions that are stored in one or more data storage units or elements (such as one or more memories), in order to process data. For example, the occupancy detection control unit 114 includes or is coupled to one or more memories. In at least one embodiment, the data storage units store data or other information as desired or needed. As an example, the data storage units are in the form of an information source or a physical memory element within a processing machine.

The set of instructions include various commands that instruct the occupancy detection control unit 114 as a processing machine to perform specific operations such as the methods and processes of the various embodiments of the subject matter described herein. In at least one embodiment, the set of instructions is in the form of a software program. For example, the software is in various forms such as system software or application software. Further, in at least one embodiment, the software is in the form of a collection of separate programs, a program subset within a larger program or a portion of a program. In at least one embodiment, the software also includes include modular programming in the form of object-oriented programming. In at least one embodiment, the processing of input data by the processing machine is in response to user commands, or in response to results of previous processing, or in response to a request made by another processing machine.

The diagrams of embodiments herein illustrate one or more control or processing units, such as the occupancy detection control unit 114. It is to be understood that, in at least one embodiment, the processing or control units represent circuits, circuitry, or portions thereof that may be implemented as hardware with associated instructions (e.g., software stored on a tangible and non-transitory computer readable storage medium, such as a computer hard drive, ROM, RAM, or the like) that perform the operations described herein. In at least one embodiment, the hardware includes state machine circuitry hardwired to perform the functions described herein. In at least one other embodiment, the hardware includes electronic circuits that include or are connected to one or more logic-based devices, such as microprocessors, processors, controllers, or the like. In at least one other embodiment, the occupancy detection control unit 114 represents processing circuitry such as one or more of a field programmable gate array (FPGA), application specific integrated circuit (ASIC), microprocessor(s), or the like. The circuits in various embodiments are configured to execute one or more algorithms to perform functions described herein. The one or more algorithms include aspects of embodiments disclosed herein, whether or not expressly identified in a flowchart or a method.

As used herein, the terms "software" and "firmware" are interchangeable, and include any computer program stored in a data storage unit (for example, one or more memories) for execution by a computer, including RAM memory, ROM memory, EPROM memory, EEPROM memory, and non-volatile RAM (NVRAM) memory. The above data storage unit types are exemplary only, and are thus not limiting as to the types of memory usable for storage of a computer program.

Figure 3:
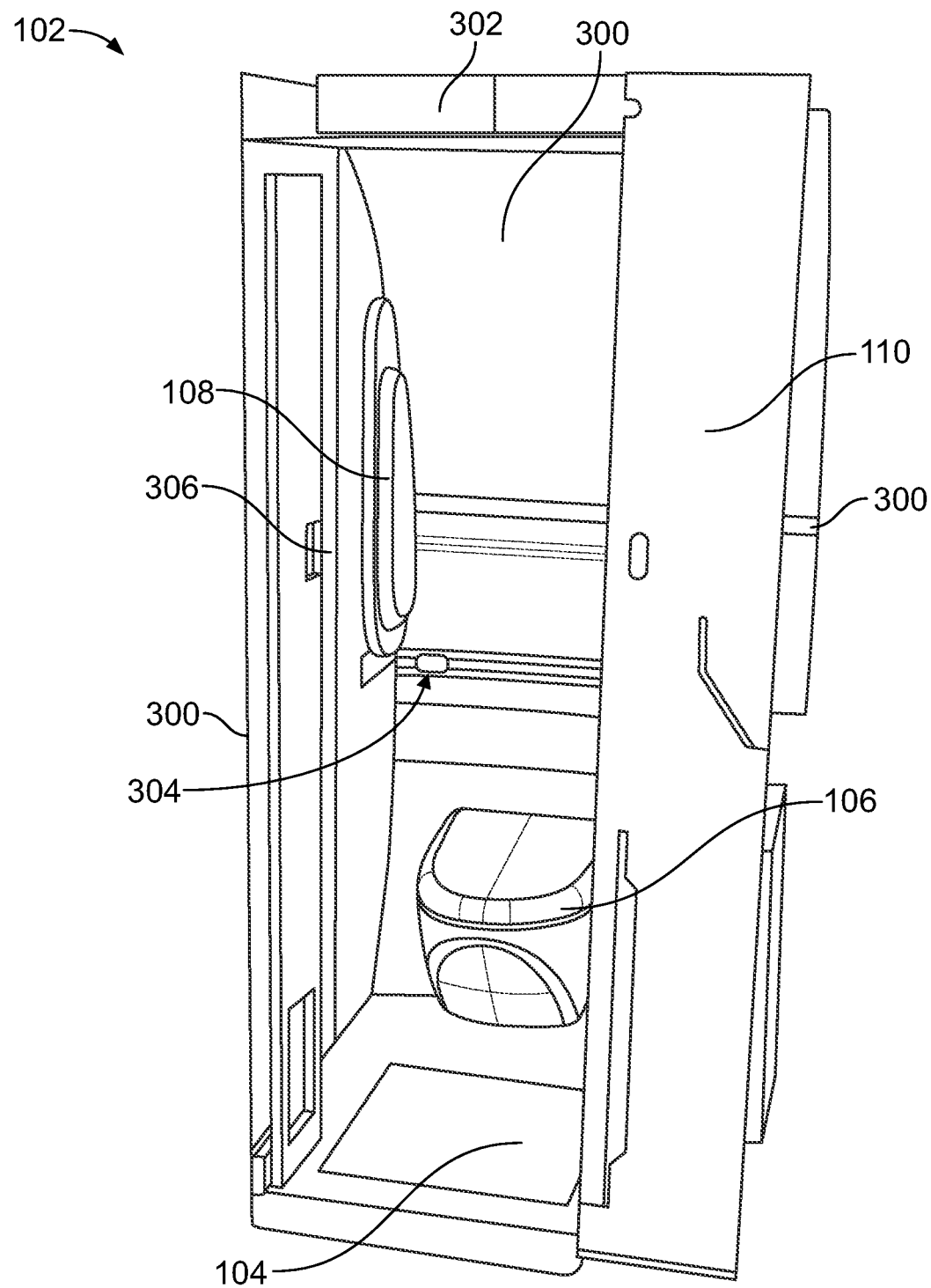
FIG. 3 illustrates a perspective front view of the lavatory, according to an embodiment of the present disclosure.

FIG. 3 illustrates a perspective front view of the lavatory 102, according to an embodiment of the present disclosure. The lavatory 102 includes walls 300, a ceiling 302, and the floor 104, which define an interior chamber 304. The toilet 106 is supported over the floor 104. The changing table 108 is positioned on an interior surface 306 of a wall 300. As shown in FIG. 3, the changing table 108 is in an upright, stowed position. The door 110 is moveably coupled to a frame, which is coupled to at least one of the walls 300, the ceiling 302, and the floor 104. A shown in FIG. 3, the door 110 is in an open position.

Figure 4:
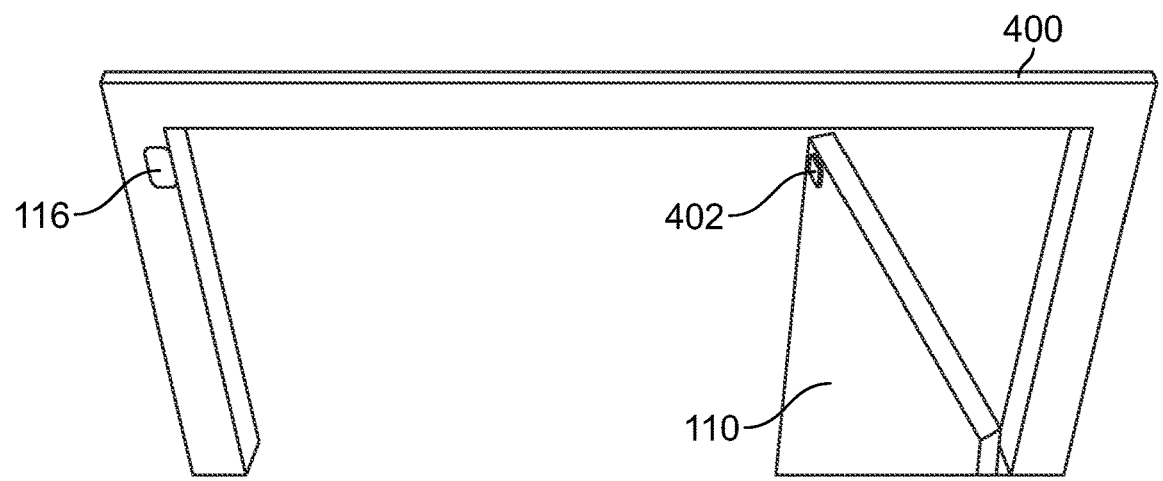
FIG. 4 illustrates a perspective top view of a door in an open position, according to an embodiment of the present disclosure.
Figure 5:
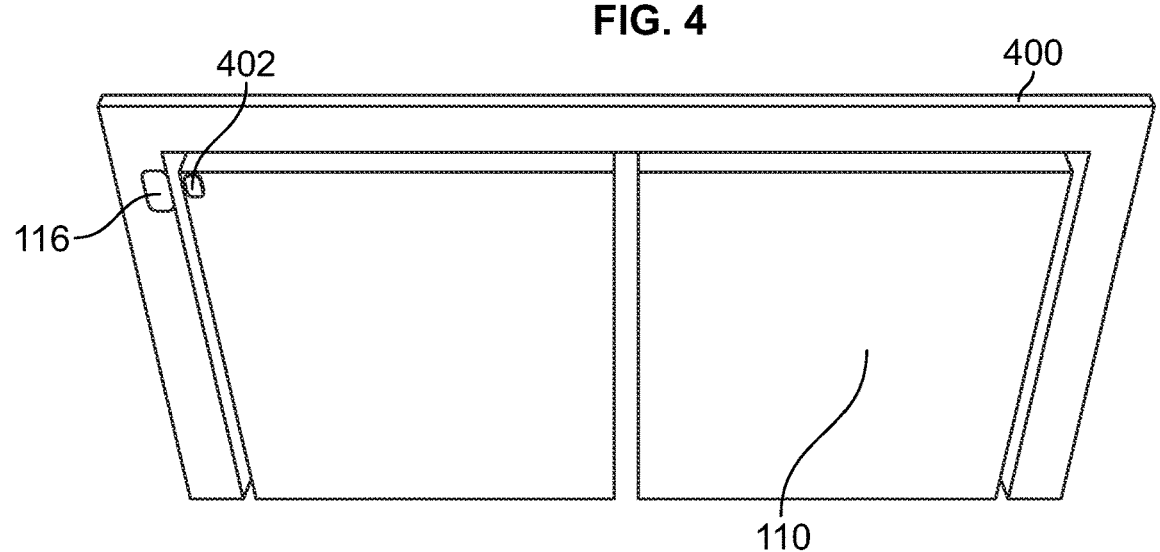
FIG. 5 illustrates a perspective view of the door in a closed position.

FIG. 4 illustrates a perspective top view of the door 110 in an open position, according to an embodiment of the present disclosure. FIG. 5 illustrates a perspective view of the door 110 in a closed position. Referring to FIGS. 4 and 5, the door 110 is coupled to a frame 400. In at least one embodiment, the door sensor 116 is a proximity sensor that is configured to detect a portion 402 (such as a piece of metal) of the door 110 within a detection range, such as when the door 110 is closed.

Figure 6:
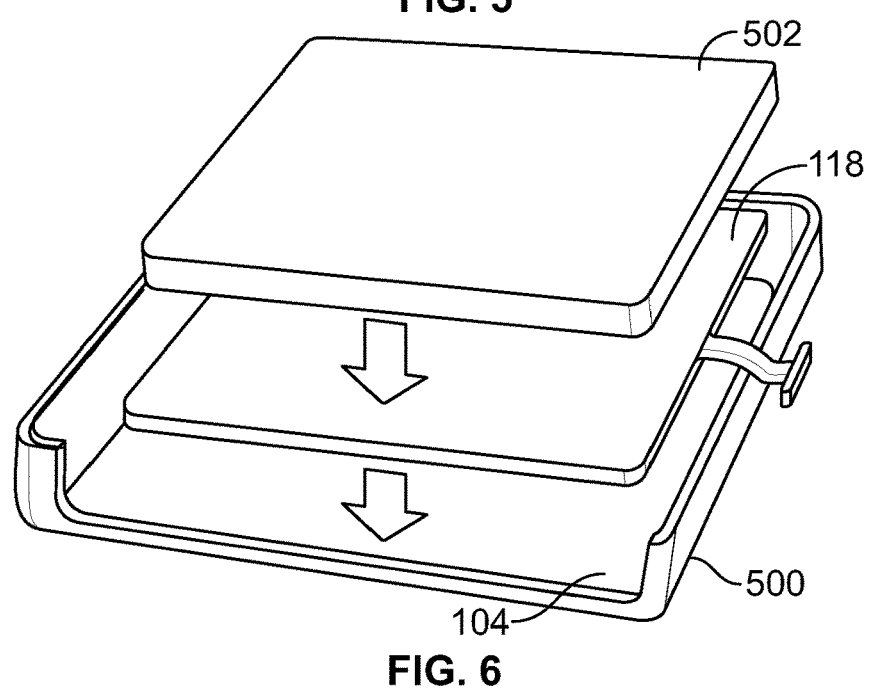
FIG. 6 illustrates a perspective top exploded view of a floor sensor coupled to a floor, according to an embodiment of the present disclosure.

FIG. 6 illustrates a perspective top exploded view of the floor sensor 118 coupled to the floor 104, according to an embodiment of the present disclosure. In at least one embodiment, the floor sensor 118 is a pressure sensor, such as a mat that is configured to detect exerted pressure, such as weight of an individual standing on the floor 104. As an example, the floor sensor 118 is sandwiched between portions of the floor 104. For example, the floor sensor 118 is disposed between a floor basin 500 and an upper floor pan 502. In at least one other embodiment, the floor sensor 118 is a proximity sensor, a temperature sensor, or the like.

Figure 7:
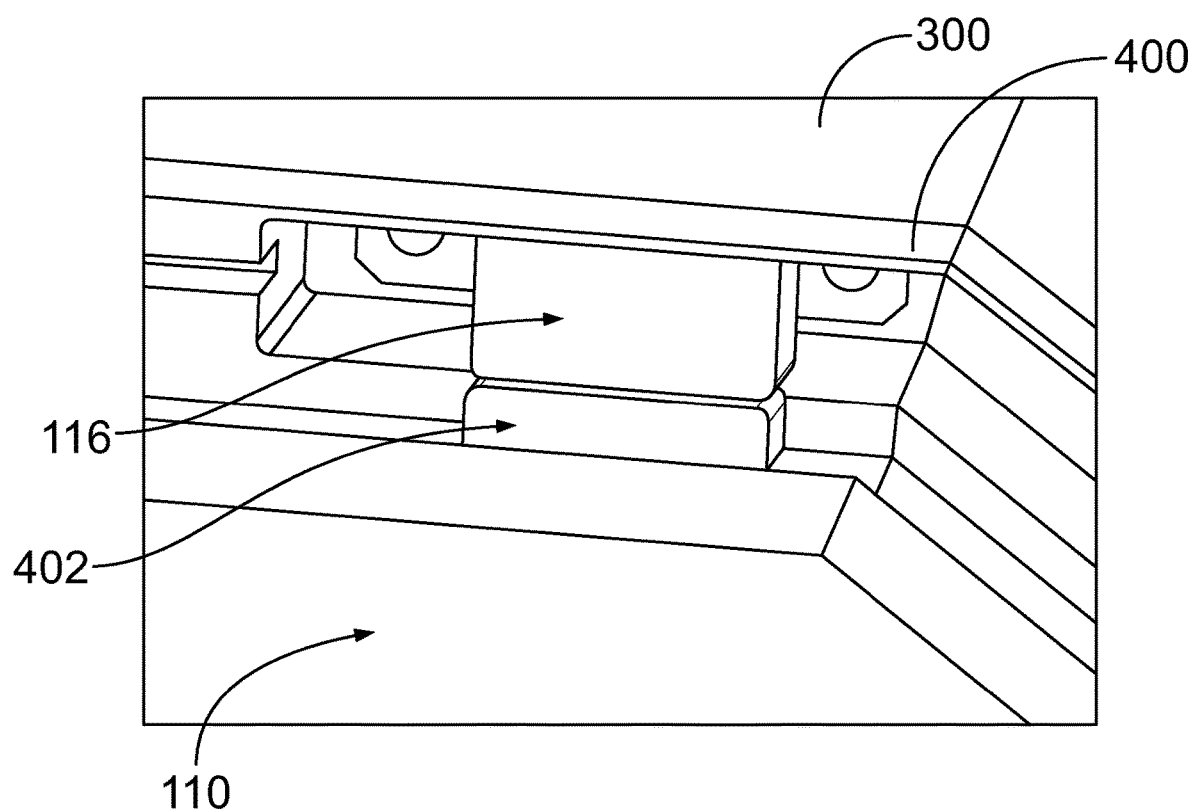
FIG. 7 illustrates a perspective view of a door sensor coupled to a frame connected to a wall, according to an embodiment of the present disclosure.

FIG. 7 illustrates a perspective view of the door sensor 116 coupled to the frame 400 connected to a wall 300, according to an embodiment of the present disclosure. In at least one embodiment, the portion 402 of the door 110 is a target material, such as a ferromagnetic material. In at least one embodiment, the door sensor 116 is akin to a Hall sensor that is configured to detect the presence of the portion 402 within a detection range. In at least one embodiment, the detection range is a distance between the door sensor 116 and the portion 402 when the door 110 is closed.

Figure 8:
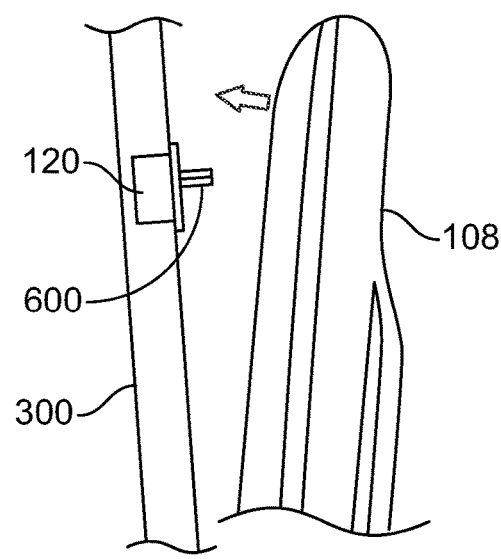
FIG. 8 illustrates a lateral view of a portion of a changing table separated from a wall, according to an embodiment of the present disclosure.

FIG. 8 illustrates a lateral view of a portion of the changing table 108 separated from a wall 300, according to an embodiment of the present disclosure. In at least one embodiment, the changing table sensor 120 includes a plunger 600 that is outwardly spring-biased, for example. When the changing table 108 is extended away from the wall 300, the plunger 600 does not contact the changing table sensor 120 and is outwardly extended, thereby breaking a circuit, as shown in FIG. 8, and outputs an extended position of the changing table 108 (for example, a presence signal indicating that the changing table 108 is in use). When the changing table 108 is stowed against the wall 300, the plunger 600 is inwardly pressed, thereby completing the circuit, and outputs a stowed position of the changing table 108 (for example, a presence signal indicating that the changing table 108 is not in use). In at least one other embodiment, the changing table sensor 120 is a proximity sensor, a pressure sensor, a temperature sensor, or the like.

Figure 9:
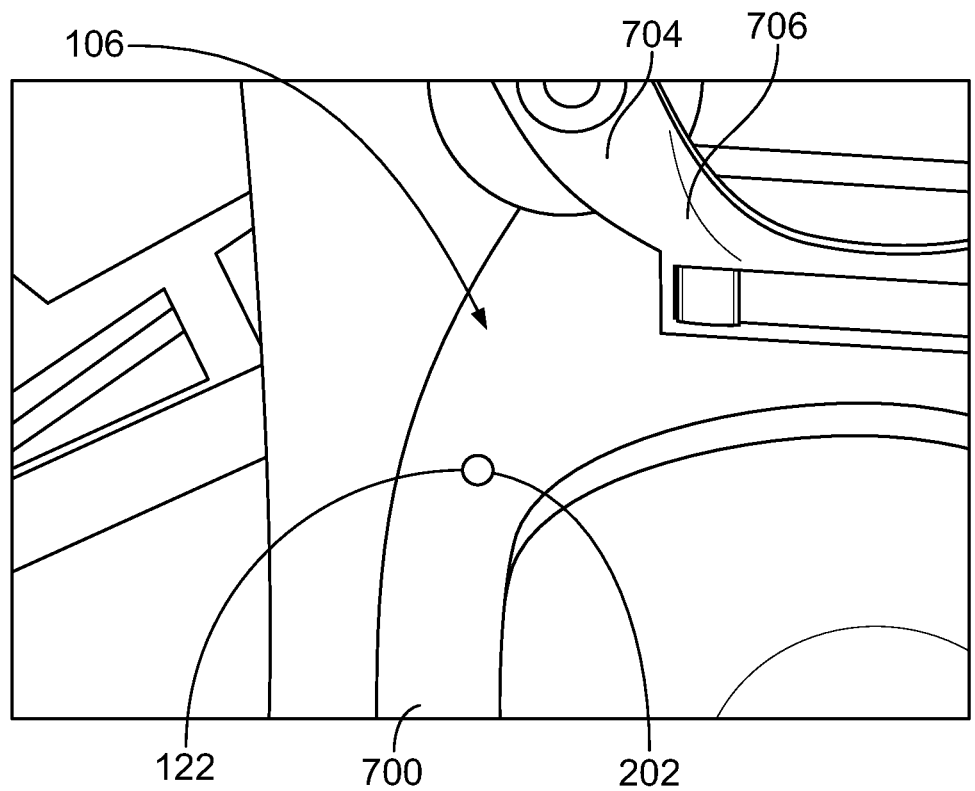
FIG. 9 illustrates a perspective top view of a toilet sensor coupled to a basin of a toilet, according to an embodiment of the present disclosure.

FIG. 9 illustrates a perspective top view of the toilet sensor 122 coupled to a basin 700 of the toilet 106 according to an embodiment of the present disclosure. In at least one embodiment, the toilet sensor 122 includes a spring-biased actuator 702, such as a plunger, extending upwardly from the basin 700 towards an underside 704 of a seat 706. When an individual is not seated on the seat 706, an internal resistance of the actuator 702 biases the seat 706 in a slightly ajar position. In this position, the toilet sensor 122 outputs a toilet sensor signal indicating that no one is seated on the toilet 106. For example, the toilet sensor 122 is an open circuit in such a position. When pressure is exerted on the seat into the actuator 702, the internal resistance is overcome, a circuit is completed, and the toilet sensor 122 outputs a presence signal (that is, a toilet sensor signal) indicating that an individual is exerting pressure onto the seat 706, and therefore an individual is within the lavatory. In at least one other embodiment, the toilet sensor 122 is a proximity sensor, a pressure sensor, a temperature sensor, or the like to trigger a signal indicating that the lavatory is occupied.

Figure 10:
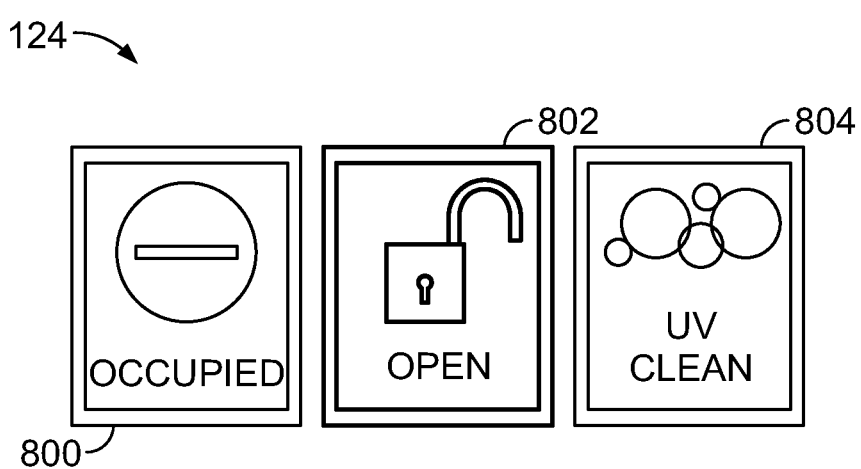
FIG. 10 illustrates a front view of an occupancy indicator, according to an embodiment of the present disclosure.

FIG. 10 illustrates a front view of the occupancy indicator 124, according to an embodiment of the present disclosure. In at least one embodiment, the occupancy indicator 124 includes one or more backlights behind an occupied indication 800, an open indication 802, and a cleaning indication 804. In at least one other embodiment, the occupancy indicator 124 does not include the cleaning indication 804. The occupied indication 800 is illuminated when the lavatory 102 (shown in FIGS. 1 and 3) is occupied. The open indication 802 is illuminated when the lavatory 102 is open (that is, unoccupied). The cleaning indication 804 is illuminated when a cleaning process is in progress. In at least one embodiment, the occupied indication 800, the open indication 802, and the cleaning indication 804 include at least one of text, graphics, and the like. In at least one other embodiment, the occupied indication 800 is an illuminated red light, and the open indication 802 is an illuminated green light, for example.

Figure 11:
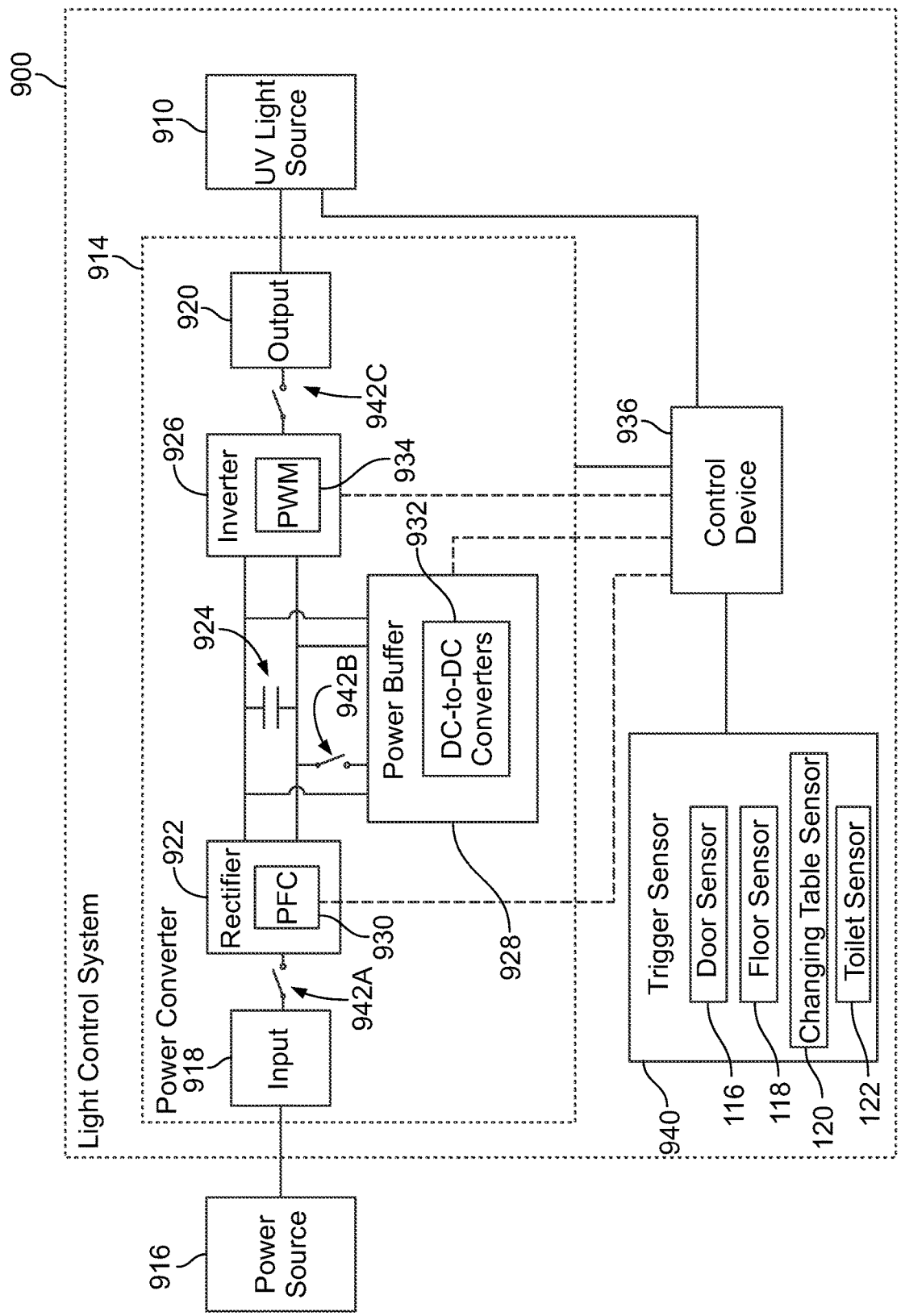
FIG. 11 illustrates a simplified block diagram of a light control system, according to an embodiment of the present disclosure.

FIG. 11 illustrates a simplified block diagram of a light control system 900, according to an embodiment of the present disclosure. In at least one embodiment, the light control system 900 includes the occupancy detection system 100, shown in FIG. 1, or portions thereof. In at least one embodiment, the occupancy detection control unit 114 shown in FIG. 1 includes circuitry as shown in FIG. 11. For example, in at least one embodiment, the occupancy detection control unit 114 includes the control device 936, shown in FIG. 11, or vice versa. In at least one other embodiment, the occupancy detection system 100 is not part of the light control system 900, or vice versa.

As shown in FIG. 11, the light control system 900 includes an ultraviolet (UV) UV light source 910, which, in at least one embodiment, is part of the cleaning system 126 shown in FIG. 1. When activated, the UV light source 910 emits UV light 912 to provide a target level of antimicrobial efficacy. For instance, the UV light source 910 emits the UV light at a predetermined wavelength and intensity for a predetermined exposure time to achieve the target level of antimicrobial efficacy during an activation cycle. In one example, the UV light source 910 emits the UV light at an intensity of 10 mW/cm2 for an exposure time of 10 seconds to achieve the target level of antimicrobial efficacy for the activation cycle.

Also, as examples, the UV light source 910 includes one or more excimer bulbs, mercury-vapor lamps, downshifting phosphor lamps, excimer lasers, organic light emitting diodes (OLEDs), and light emitting diodes (LEDs). More generally, in at least one embodiment, the UV light source 910 is a light source that emits the UV light at a wavelength within the UV spectrum (i.e., between approximately 10 nanometers (nm) and approximately 400 nm). In some implementations, the UV light source 910 is a light source that emits UV light at a wavelength within the far-UV spectrum (e.g., between approximately 190 nm and approximately 240 nm). For instance, in one implementation, the UV light source 910 is a light source that emits the UV light at a wavelength of approximately 222 nm. By emitting the UV light at a wavelength in the far-UV spectrum, the UV light source 910 more rapidly disinfects the environment than by emitting the UV light at other wavelengths in the UV spectrum.

As shown in FIG. 11, the light control system 900 also includes a power converter 914 coupled to the UV light source 910. The power converter 914 receives an input power from a power source 916 at an input 918 and outputs a supply power to the UV light source 910 at an output 920. As an example, the power source 916 provides the input power as an alternating-current (AC) power. In one implementation, the power source 916 provides the input power as a three-phase AC power with a voltage of 115 volts (V) and a frequency of 400 Hertz (Hz). For instance, in a vehicle, the power source 916 includes an engine turbine that generates electrical energy and an electrical distribution system that provides the generated electrical energy to the light control system 900 in the form of the input power. Other example power sources 916 are also possible.

The power converter 914 converts the input power into the supply power. Within examples, the supply power has a different AC waveform than the input power. For instance, the supply power has a different frequency, voltage, or current than the input power. More generally, in at least one embodiment, the supply power has a wattage that is greater than a wattage of the input power. As such, the power converter 914 provides the UV light source 910 with the supply power, which is sufficient to emit the UV light at the target level of antimicrobial efficacy. In one example, the input power has a wattage that is less than 1 kW and the supply power has a wattage that is equal to or greater than 1 kW.

In FIG. 11, the power converter 914 includes the input 918, a rectifier 922, a direct current (DC) link 924, an inverter 926, a power buffer 928, and the output 920. The rectifier 922 is coupled to and receives the input power from the input 918. The rectifier 922 converts the AC input power into a DC power. In an example, the rectifier 922 includes a power factor corrector (PFC) 930 that corrects a power factor of the input power to facilitate more efficient use of the input power by the light control system 900. The PFC 930 also facilitates isolating the light control system 900 from the power source 916 (or other electrical subsystems coupled to the power source 916). Within examples, the PFC 930 includes a passive PFC circuit, an active PFC circuit, or a dynamic PFC circuit.

The rectifier 922 is coupled to the inverter 926 via the DC link 924. As described in further detail below, when the UV light source 910 is activated, the inverter 926 converts the DC power received from the rectifier 922 into an AC power, which provides a portion of the supply power at the output 920. The DC link 924 facilitates the coupling of the rectifier 922 and the inverter 926. In one example, the DC link 924 includes a capacitor coupled in parallel between the rectifier 922 and the inverter 926. The DC link 924 assists in mitigating transients propagating toward the power source 916 or assists in smoothing pulses in the rectified DC power provided by the rectifier 922.

As shown in FIG. 11, the power buffer 928 is coupled in parallel between the rectifier 922 and the DC link 924, and between the DC link 924 and the inverter 926. The power buffer 928 stores power using the input power received at the input 918 when the UV light source 910 deactivated. As examples, the power buffer 928 includes a battery, a capacitor, or another type of energy storage device.

In the example of FIG. 11, the power buffer 928 includes a plurality of DC-to-DC converters 932 coupled to each other. When the UV light source 910 is deactivated, the DC-to-DC converters 932 receive the DC power from the rectifier 922. In one implementation, the DC-to-DC converters 932 include a first DC-to-DC converter that steps down the DC power received from the rectifier 922 and a second DC-to-DC converter that steps up the DC power. This configuration of the DC-to-DC converters 932 beneficially reduces (or minimizes) the size or weight of the power buffer 928.

As noted above, the inverter 926 is coupled to the rectifier 922 and the power buffer 928. In this arrangement, when the UV light source 910 is activated, the inverter 926 receives the DC power from the rectifier 922 and the power stored in the power buffer 928. The inverter 926 converts this combination of DC power from the rectifier 922 and the power buffer 928 into the supply power, which has an AC waveform. In an example, the inverter 926 includes a pulse-width modulator (PWM) 934, which switches on and off to control a frequency of the supply power. In another example, the inverter 926 additionally or alternatively includes one or both of a sine wave generator and a carrier wave generator to convert the combination of DC power to the supply power.

As further shown in FIG. 11, in at least one embodiment, the light control system 900 also includes a control device 936 communicatively coupled to the power converter 914 and one or more trigger sensors 940. In at least one embodiment, the control device 936 is or otherwise includes the occupancy detection control unit 114, shown in FIG. 1, or vice versa. In at least one embodiment, the trigger sensors 940 include one or more of the door sensor 116, the floor sensor 118, the changing table sensor 120, or the toilet sensor 122, as described with respect to FIG. 1. In general, the control device 936 communicates with the trigger sensor(s) 940 to receive information related to the operation of the light control system 900 (or the occupancy detection system 100, shown in FIG. 1) or communicate with the power converter 914 to control operation of the light control system 900 based on the information received from the light sensor 938 or the trigger sensor(s) 940. In at least one embodiment, the control device 936 additionally or alternatively incorporates in the light sensor 938, the trigger sensor(s) 940, or other components of the light control system 900.

In some examples, the control device 936 controls the operation of the light control system 900 by activating the UV light source 910. For instance, in one example, the trigger sensor(s) 940 detects one or more trigger conditions and responsively generate a trigger-sensor signal indicating that the trigger condition(s) were detected. The control device 936 receives the trigger-sensor signal indicating that the trigger condition was detected, determines, based on the trigger-sensor signal, that one or more criteria are met, and responsive to the determination that the one or more criteria are met, transmits a control signal to activate the UV light source 910.

In at least one embodiment, in response to the receiving presence sensor signals from the triggers sensors 940, the control device 936 controls at least one of the rectifier 922, the power buffer 928, and the inverter 926 to prevent the UV light source 910 from emitting UV light. For example, in response to receiving a door sensor signal from the door sensor 116 indicating that the door 110 (shown in FIG. 1) is open, the control device 936 controls the operation of at least one of the rectifier 922, the power buffer 928, the inverter 926, and switches 942A, 942B, or 942C to ensure that the UV light source 910 does not emit UV light. As another example, in response to receiving a floor sensor signal from the floor sensor 116 indicating that presence of an individual on the floor 104 (shown in FIG. 1), the control device 936 controls the operation of at least one of the rectifier 922, the power buffer 928, the inverter 926, and switches 942A, 942B, or 942C to ensure that the UV light source 910 does not emit UV light. As another example, in response to receiving a changing table sensor signal from the changing table sensor 120 indicating that presence on the changing table 108 (shown in FIG. 1) is open, the control device 936 controls operation of at least one of the rectifier 922, the power buffer 928, the inverter 926, and switches 942A, 942B, or 942C to ensure that the UV light source 910 does not emit UV light. As another example, in response to receiving a toilet sensor signal from the toilet sensor 122 indicating that presence on the toilet 106 (shown in FIG. 1) is open, the control device 936 controls operation of at least one of the rectifier 922, the power buffer 928, the inverter 926, and switches 942A, 942B, or 942C to ensure that the UV light source 910 does not emit UV light.

As described herein, in at least certain embodiments, the trigger sensor(s) 940 (including at least one of the door sensor 116, the floor sensor 118, the changing table sensor 120, and the toilet sensor 122) include a motion sensor, an occupancy sensor, a thermal sensor, a door open/close sensor, an infrared sensor device, an ultrasonic sensor device, a floor pressure sensor, or other types of sensors, as described above with respect to FIGS. 1-10. For instance, in an example in which the light control system 900 is located on a vehicle having a lavatory, the trigger condition(s) detected by the trigger sensor(s) 940 includes at least one of a door of the lavatory being opened, the door of the lavatory being closed, the lavatory being occupied, and the lavatory being unoccupied. Additionally, for example, the one or more criteria that is used by the control device 936 to determine whether to activate the UV light source 910 includes one or more criterion such as a door of the lavatory being closed, the lavatory being unoccupied, the lavatory having been occupied a predetermined number of times since a previous activation of the UV light source 910, and a predetermined amount of time having passed since the previous activation of the UV light source 910.

In an additional or alternative example, the trigger sensor(s) 940 includes a user input device that is actuatable by an operator. As examples, the user input device includes one or more buttons, a mouse, keypads, keyboards, or switches. Responsive to the operator actuating the user input device, the user input device transmits the trigger-sensor signal to the control device 936 to cause the control device 936 to transmit the control signal to the power converter 914 for activating the UV light source 910. In this way, the trigger sensor(s) 940 provide for on-demand actuation of the light control system 900 to disinfect a given environment (e.g., a hospital room or an aircraft lavatory).

In some examples, the control device 936 control the operation of the light control system 900 by deactivating the UV light source 910 in response to presence sensor signals received from the door sensor 116, the floor sensor 118, the changing table sensor 120, or the toilet sensor 122. In at least one embodiment, the control device 936 deactivates the UV light source 910 to prevent (or delay) a future activation cycle or to terminate a current activation cycle (i.e., to override a decision, based on a trigger-sensor signal, to activate the UV light source 910) in response to receiving a presence sensor signal indicating presence of an individual within an enclosed space or a door sensor signal indicating that the door 110 is open.

Within examples, the control device 936 deactivates the UV light source 910 responsive to an occurrence of one or more override conditions to enhance (or maximize) operational safety or reduce (or minimize) operational transients. In general, the override conditions include, for example, conditions relating to presence of an individual within an enclosed space (such as the lavatory 102 shown in FIG. 1), the door 110 of the lavatory 102 being open, conditions relating to one or more components of the light control system 900 (e.g., a temperature of a component of the light control system 900 or an amount of energy stored in the power buffer 928) or conditions relating to an environment in which the component(s) of the light control system 900 are located (e.g., a temperature of the environment or an occupancy of the environment). As further examples, the override conditions additionally or alternatively include conditions relating to an occurrence of an emergency state of one or more devices external to the light control system 900 (e.g., an emergency state of one or more devices on an aircraft or in a hospital), or an occurrence of an attempt to tamper with one or more components of the light control system 900. In at least one embodiment, a load shed (such as when power from an aircraft is diverted to flight critical systems in an emergency situation) automatically deactivates the UV light source 910. As another example, a load balancing (such as when too many lamps are activated at the same time) also automatically deactivates the UV light source 910.

In one implementation, the trigger sensor(s) 940 (such as the door sensor 116, the floor sensor 118, the changing table sensor 120, and the toilet sensor 122) detect the override condition(s) (for example, presence of an individual within the lavatory 102) and responsively generate an override-sensor signal indicating that the override condition(s) were detected. The control device 936 receives the override-sensor signal indicating that the override condition(s) were detected, determines, based on the override-sensor signal, that one or more criteria are met, and responsive to the determination that the one or more criteria are met, transmit a control signal to deactivate the UV light source 910.

In one example, the trigger sensor(s) 940 (for example, the door sensor 116) detects when the door 110 opens or a person enters a vicinity of the light control system 900, and the control device 936 responsively causes the light control system 900 to deactivate as a security or safety feature. Additionally, for instance, when the door 110 subsequently closes or the person subsequently leaves the vicinity of the light control system 900, the trigger sensors 940 transmit the trigger-sensor signal to the control device 936 to activate the light control system 900 or prepare the light control system 900 to be activated responsive to a next trigger-sensor signal from the trigger sensor(s) 940.

In some examples, the control device 936 transmits the control signal to the power converter 914 to deactivate the UV light source 910. For instance, in one implementation, the control device 936 transmits the control signal to one or more switches 942A-942C to actuate the switch(es) 942A-942C from a closed state to an open state to deactivate the component(s) of the light control system 900 downstream of the switch(es) 942A-942C. In the closed state, each switch 942A-942C conducts power through the switch 942A-942C. Whereas, in the open state, each switch 942A-942C inhibits or prevents power transmission through the switch 942A-942C (e.g., actuate the switches 942A-942C to prevent the UV light source 910 from receiving the supply power).

In FIG. 11, for instance, the switches 942A-942C include a first switch 942A located at any point between the input 918 and the rectifier 922, a second switch 942B located at any point between the rectifier 922 and the power buffer 928, and a third switch 942C located at any point between the inverter 926 and the UV light source 910 (e.g., the output 920). In this arrangement, the control device 936 selectively transmits the control signal to one or more of the switches 942A-942C to specifically deactivate the components of the light control system 900 downstream of those switches 942A-942C. This allows the control device 936 to selectively deactivate different portions of the light control system 900 based on the specific override condition detected, such as detected presence of an individual within the lavatory 102, as detected by at least one of the door sensor 116, the floor sensor 118, the changing table sensor 120, and the toilet sensor 122.

For instance, as one example, in a situation in which an override condition occurs with respect to the UV light source 910, the power buffer 928 continues to store power (e.g., charge up) while the override condition is resolved for the UV light source 910. This allows for more rapid activation of the UV light source 910 using the power stored in the power buffer 928 when the override condition is resolved. In FIG. 11, the control device 936 transmits the control signal to the third switch 942C to actuate the third switch 942C to the open state while the first switch 942A and the second switch 942B remain in the closed state. As such, the power buffer 928 continues to receive power from the rectifier 922 while the output 920 and the UV light source 910 are disconnected from the inverter 926 (and, thus, deactivated).

Although three switches 942A-942C are depicted in FIG. 11, in at least one embodiment, the light control system 900 includes a lesser quantity or a greater quantity of switches 942A-942C at additional or alternative locations within the light control system 900 in other example embodiments. For instance, in another example, the switch(es) 942A-942C are additionally or alternatively provided in the rectifier 922, in the inverter 926, in the power buffer 928, at a point before the input 918, at a point after the output 920, or any other point between the power source 916 and the output 920. This beneficially allows for greater options of deactivating the select components of the light control system 900. Specifically, the trigger sensor(s) 940 and the control device 936 operate in a similar manner to that described above to selectively deactivate at least one of the rectifier 922, the PFC 930, the inverter 926, and the PWM 934 responsive to detecting an occurrence of an override condition in connection with the component(s) to be deactivated.

In response to the control device 936 deactivating the UV light source 910, the control device 936 (for example, the occupancy detection control unit 114) deactivate the cleaning indication 804 of the occupancy indicator 124, shown in FIG. 10. For example, when the UV light source 910 is active and emitting UV light, the cleaning indication 804 is illuminated. As the UV light source 910 is deactivated, the illumination of the cleaning indication 804 ceases.

Figure 12:
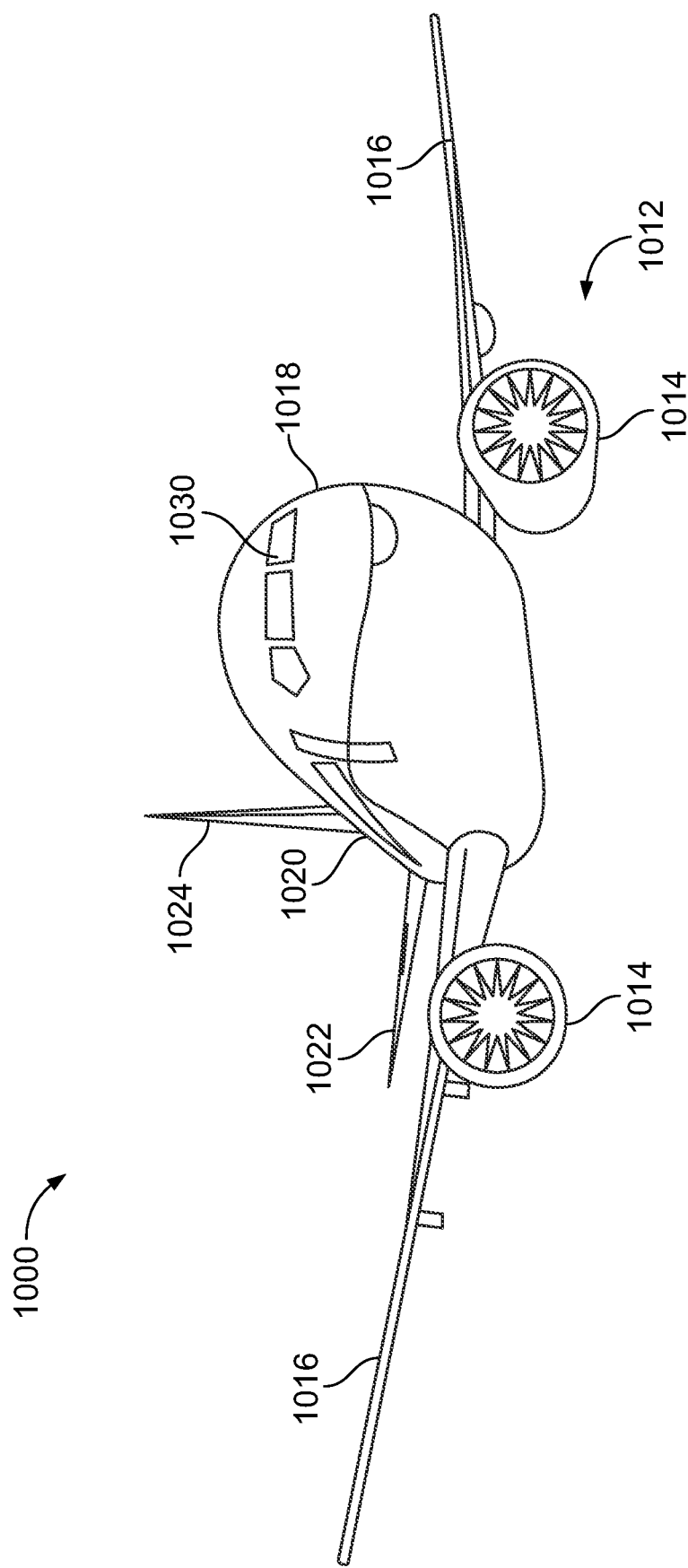
FIG. 12 illustrates a front perspective view of an aircraft, according to an exemplary embodiment of the present disclosure.

FIG. 12 illustrates a front perspective view of an aircraft 1000, according to an exemplary embodiment of the present disclosure. The aircraft 1000 includes a propulsion system 1012 that includes two turbofan engines 1014, for example. As another example, the propulsion system 1012 includes more engines 1014 than shown. The engines 1014 are carried by wings 1016 of the aircraft 1000. In other embodiments, the engines 1014 are carried by a fuselage 1018 or an empennage 1020. In at least one embodiment, the empennage 1020 also supports horizontal stabilizers 1022 and a vertical stabilizer 1024. The fuselage 1018 of the aircraft 1000 defines an interior cabin, which includes a cockpit 1030, for example.

The interior cabin includes one or more lavatories, such as the lavatory 102 shown in FIGS. 1 and 3. An occupancy detection system, such as the occupancy detection system 100 shown in FIG. 1, and a light control system, such as the light control system 900 shown in FIG. 11, are used with respect to one or more of the lavatories within the interior cabin. Certain embodiments of the present disclosure are used with various other vehicles other than aircraft. For example, embodiments of the present disclosure are used with land-based vehicle (such as buses), watercraft (such as cruise ships), or the like.

Referring to FIGS. 1-12, embodiments of the present disclosure provide occupancy detection systems and methods, which are used with respect to lavatories of vehicles, fixed structures (such as buildings), or the like. Embodiments of the present disclosure provide systems and methods for accurately determining whether or not a lavatory, such as within a commercial aircraft, is occupied. Further, embodiments of the present disclosure provide systems and methods for determining the occupancy of a lavatory without an individual performing a specific task to indicate such occupancy. Moreover, embodiments of the present disclosure provide systems and methods for quickly and efficiently determining an occupancy status of a lavatory.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

The invention claimed is:

1. An occupancy detection system for an enclosed space, the occupancy detection system comprising:
　　a door sensor operatively coupled to a door of the enclosed space, wherein the door sensor is configured to output a door sensor signal that indicates a status of the door;
　　at least one presence sensor that is configured to output at least one presence sensor signal that indicates an occupancy status of the enclosed space;

an occupancy detection control unit in communication with the door sensor and the at least one presence sensor; and an occupancy indicator in communication with the occupancy detection control unit, wherein the occupancy status of the enclosed space is indicated by the occupancy indicator, and wherein in response to a UV light source being deactivated, the occupancy detection control unit deactivates a cleaning indication of the occupancy indicator.

2. The occupancy detection system of claim 1, wherein the occupancy detection control unit determines that the enclosed space is unoccupied in response to the door sensor signal indicating that the door is open.

3. The occupancy detection system of claim 1, wherein the door sensor signal indicating that the door is open triggers the occupancy detection control unit to perform a reading of the at least one presence sensor signal.

4. The occupancy detection system of claim 1, wherein the door sensor comprises one or more of a proximity sensor, a pressure sensor, or a temperature sensor.

5. The occupancy detection system of claim 1, wherein the at least one presence sensor comprises one or more of a proximity sensor, a pressure sensor, or a temperature sensor.

6. The occupancy detection system of claim 1, wherein the at least one presence sensor comprises a floor sensor operatively coupled to a floor of the enclosed space, and wherein the at least one presence sensor signal comprises a floor sensor signal output by the floor sensor.

7. The occupancy detection system of claim 1, wherein the at least one presence sensor comprises a changing table sensor operatively coupled to a changing table of the enclosed space, and wherein the at least one presence sensor signal comprises a changing table sensor signal output by the changing table sensor.

8. The occupancy detection system of claim 1, wherein the at least one presence sensor comprises a plurality of presence sensors including:
  a floor sensor operatively coupled to a floor of the enclosed space, wherein the at least one presence sensor signal comprises a floor sensor signal output by the floor sensor; and
  a changing table sensor operatively coupled to a changing table of the enclosed space, wherein the at least one presence sensor signal further comprises a changing table sensor signal output by the changing table sensor.

9. The occupancy detection system of claim 1, further comprising a cleaning system that is in communication with the occupancy detection control unit, wherein the cleaning system is configured to automatically clean at least a portion of the enclosed space when the door is closed and the enclosed space is unoccupied.

10. The occupancy detection system of claim 1, wherein the occupancy detection control unit is configured to respond to receiving the door sensor signal and the at least one presence sensor signal by transmitting a control signal to one or more switches to actuate the switches from a closed state to an open state to deactivate one or more components of a light control system.

11. The occupancy detection system of claim 1, wherein the occupancy detection control unit is in communication with the door of the enclosed space, and wherein the occupancy detection control unit is configured to lock the door during a cleaning process of the enclosed space.

12. The occupancy detection system of claim 1, wherein the occupancy detection control unit is configured to receive the door sensor signal and the at least one presence sensor signal.

13. The occupancy detection system of claim 1, wherein the occupancy detection control unit is configured to determine an occupancy status of the enclosed space based on the door sensor signal and the at least one presence sensor signal, wherein the occupancy detection control unit is further configured to output an occupancy signal indicative of the occupancy status of the enclosed space.

14. The occupancy detection system of claim 1, wherein the occupancy detection control unit operates the occupancy indicator based on an occupancy status of the enclosed space as determined by the occupancy detection control unit.

15. The occupancy detection system of claim 1, wherein the occupancy detection control unit determines the enclosed space is occupied in response to the door sensor signal indicating that the door is closed and the at least one presence sensor signal indicating that an individual is within the enclosed space.

16. The occupancy detection system of claim 1, wherein the occupancy detection control unit resets an occupancy status to unoccupied in response to the door sensor signal indicating that the door is opened after being closed.

17. An occupancy detection method for an enclosed space, the occupancy detection method comprising:
  operatively coupling a door sensor to a door of the enclosed space;
  communicatively coupling an occupancy detection control unit with the door sensor, at least one presence sensor of the enclosed space, and an occupancy indicator that indicates the occupancy status of the enclosed space;
  outputting, by the door sensor, a door sensor signal that indicates a status of the door;
  outputting, by the at least one presence sensor, at least one presence sensor signal that indicates an occupancy status of the enclosed space;
  receiving, by the occupancy detection control unit, the door sensor signal and the at least one presence sensor signal;
  in response to the receiving, transmitting a control signal to one or more switches to actuate the switches from a closed state to an open state to deactivate one or more components of a light control system; and
  in response to one of more components of the light control system being deactivated, deactivating a cleaning indication of the occupancy indicator.

18. The occupancy detection method of claim 17, wherein the determining comprises determining that the enclosed space is unoccupied in response to the door sensor signal indicating that the door is open.

19. The occupancy detection method of claim 17, further comprising triggering, by the door sensor signal indicating that the door is open, the occupancy detection control unit to perform a reading of the at least one presence sensor signal.

20. The occupancy detection method of claim 17, further comprising:
  communicatively coupling a cleaning system with the occupancy detection control unit; and
  automatically cleaning at least a portion of the enclosed space when the door is closed and the enclosed space is unoccupied.

21. The occupancy detection method of claim 17, further comprising:

communicatively coupling the occupancy detection control unit with the door of the enclosed space; and locking, by the occupancy detection control unit, the door during a cleaning process of the enclosed space.

22. The occupancy detection method of claim 17, further comprising:

determining, by the occupancy detection control unit, an occupancy status of the enclosed space based on the door sensor signal and the at least one presence sensor signal, wherein the determining comprises determining that the occupancy status is occupied in response to the door sensor signal indicating that the door is closed and the at least one presence sensor signal indicating that an individual is within the enclosed space.

23. The occupancy detection method of claim 17 resetting, by the occupancy detection control unit, the occupancy status to unoccupied in response to the door sensor signal indicating that the door is opened after being closed.

24. An occupancy detection system for an enclosed space, the occupancy detection system comprising:

a door sensor operatively coupled to a door of the enclosed space, wherein the door sensor is configured to output a door sensor signal that indicates a status of the door;

at least one presence sensor that is configured to output at least one presence sensor signal, wherein the at least one presence sensor comprises a changing table sensor operatively coupled to a changing table of the enclosed space, and wherein the at least one presence sensor signal comprises a changing table sensor signal output by the changing table sensor;

an occupancy detection control unit in communication with the door sensor and the at least one presence sensor; and an occupancy indicator in communication with the occupancy detection control unit, wherein the occupancy status of the enclosed space is indicated by the occupancy indicator, wherein the occupancy detection control unit is configured to determine an occupancy status of the enclosed space based on the door sensor signal and the at least one presence sensor signal, wherein the occupancy detection control unit is further configured to output an occupancy signal indicative of the occupancy status of the enclosed space, and wherein the occupancy detection control unit operates the occupancy indicator based on the occupancy status of the enclosed space as determined by the occupancy detection control unit.

25. An occupancy detection system for an enclosed space, the occupancy detection system comprising:

a door sensor operatively coupled to a door of the enclosed space, wherein the door sensor is configured to output a door sensor signal that indicates a status of the door;

at least one presence sensor that is configured to output at least one presence sensor signal;

an occupancy detection control unit in communication with the door sensor and the at least one presence sensor; and an occupancy indicator in communication with the occupancy detection control unit, wherein the occupancy status of the enclosed space is indicated by the occupancy indicator, wherein the occupancy detection control unit is configured to determine an occupancy status of the enclosed space based on the door sensor signal and the at least one presence sensor signal, wherein the occupancy detection control unit is further configured to output an occupancy signal indicative of the occupancy status of the enclosed space, wherein the occupancy detection control unit operates the occupancy indicator based on the occupancy status of the enclosed space as determined by the occupancy detection control unit, and wherein in response to a UV light source being deactivated, the occupancy detection control unit deactivates a cleaning indication of the occupancy indicator.

26. The occupancy detection system of claim 25, wherein the door sensor signal indicating that the door is open triggers the occupancy detection control unit to perform a reading of the at least one presence sensor signal.

27. An occupancy detection method for an enclosed space, the occupancy detection method comprising:

operatively coupling a door sensor to a door of the enclosed space;

communicatively coupling an occupancy detection control unit with the door sensor, at least one presence sensor of the enclosed space, and an occupancy indicator that indicates the occupancy status of the enclosed space;

outputting, by the door sensor, a door sensor signal that indicates a status of the door;

outputting, by the at least one presence sensor, at least one presence sensor signal;

determining, by the occupancy detection control unit, an occupancy status of the enclosed space based on the door sensor signal and the at least one presence sensor signal;

outputting, by the occupancy detection control unit, an occupancy signal indicative of the occupancy status of the enclosed space;

operating, by the occupancy detection control unit, the occupancy indicator based on the occupancy status of the enclosed space as determined by the occupancy detection control unit, and wherein in response to one of more components of a light control system being deactivated, deactivating a cleaning indication of the occupancy indicator.

* * * * *